US00PP34415P2

(12) United States Plant Patent
Nishikawa

(10) Patent No.: US PP34,415 P2
(45) Date of Patent: Jul. 5, 2022

(54) ***BIDENS* PLANT NAMED 'FSK17S41'**

(50) Latin Name: *Bidens ferulifolia*
Varietal Denomination: 'FSK17S41'

(71) Applicant: Koichiro Nishikawa, Waddinxveen (NL)

(72) Inventor: Koichiro Nishikawa, Waddinxveen (NL)

( * ) Notice: Subject to any disclaimer, the term of this patent is extended or adjusted under 35 U.S.C. 154(b) by 0 days.

(21) Appl. No.: 17/574,640

(22) Filed: Jan. 13, 2022

(30) Foreign Application Priority Data

Jul. 21, 2021 (QZ) ..... PBR 2021/1911

(51) Int. Cl.
*A01H 6/14* (2018.01)
*A01H 5/02* (2018.01)

(52) U.S. Cl.
USPC ..... Plt./410

(58) Field of Classification Search
USPC ..... Plt./410
See application file for complete search history.

*Primary Examiner* — Annette H Para
(74) *Attorney, Agent, or Firm* — Penny J. Aguirre

(57) ABSTRACT

A new cultivar of *Bidens* plant named 'FSK17S41' that is characterized by its large sized inflorescences, its inflorescences with ray floret colors that are yellow with orange-red centers, its moderately vigorous plant habit, and its upright to mounding plant habit.

2 Drawing Sheets

Botanical classification: *Bidens ferulifolia.*
Variety denomination: 'FSK17S41'.

CROSS-REFERENCE TO A RELATED APPLICATION

This application claims priority to European Community Plant Variety Office (CPVO) Plant Breeder's Rights Application No. 2021/1911 filed on Jul. 21, 2021, under 35 U.S.C. 119(f), the entire contents of which is incorporated by reference herein. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Bidens ferulifolia* plant, botanically known as *Bidens ferulifolia* 'FSK17S41' and will be referred to hereinafter by its cultivar name, 'FSK17S41'. The new cultivar of *Bidens* is an evergreen perennial grown for landscape and container use.

The new cultivar was derived from a controlled breeding program conducted by the Inventor in Katsuta-Gun, Okayama-Pref., Nagi-chio Gyoho, Japan. The new cultivar arose from a cross made in June of 2013 between an unnamed and unpatented proprietary plants from the Inventor's breeding program; reference no. F1218 as the female parent and ref no. F1213 as the male parent. The Inventor selected 'FSK17S41' in October of 2014 as a single unique plant amongst the seedlings that resulted from the above cross.

Asexual propagation of the new cultivar was first accomplished by stem cuttings in March of 2015 by the Inventor in Katsuta-Gun, Okayama-Pref., Nagi-chio Gyoho, Japan. Asexual propagation by stem cuttings has determined the characteristics of the new cultivar are stable and reproduced true to type in successive generations.

SUMMARY OF THE INVENTION

The following traits have been repeatedly observed and are determined to be the characteristics of the new cultivar. These attributes in combination distinguish 'FSK17S41' as a unique cultivar of *Bidens*.

1. 'FSK17S41' exhibits large sized inflorescences.
2. 'FSK17S41' exhibits inflorescences with ray floret colors that are yellow with orange-red centers.
3. 'FSK17S41' exhibits a moderately vigorous plant habit.
4. 'FSK17S41' exhibits an upright to mounding plant habit.

The female parent differs from 'FSK17S41' in having a larger inflorescences with ray florets that have a smaller red center and a more mounding plant habit. The male parent differs from 'FSK17S41' in having smaller inflorescences and a more vigorous growth habit. 'FSK17S41' can also be compared to the *Bidens* cultivar 'Golden Empire' (not patented). 'Golden Empire' differs from 'FSK17S41' in having a medium sized inflorescences with ray florets that are solid yellow in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by West Madison, Syngenta Flowers, Young's Plant Farm, Greenhouse Canada, Nursery Mag, Beichel, Griffins, Bill Moore Co, Al's Garden Center, BallHort, JVK.

BRIEF DESCRIPTION OF THE DRAWINGS

The accompanying color photographs illustrate the overall appearance and distinct characteristics of the new *Bidens*. The photographs were taken of an 11-week-old plant of 'FSK17S41' as grown in a greenhouse in a 12-cm container in Andijk, The Netherlands.

The photograph in FIG. 1 provides a side view of the plant habit of 'FSK17S41' in bloom.

Figure 1:
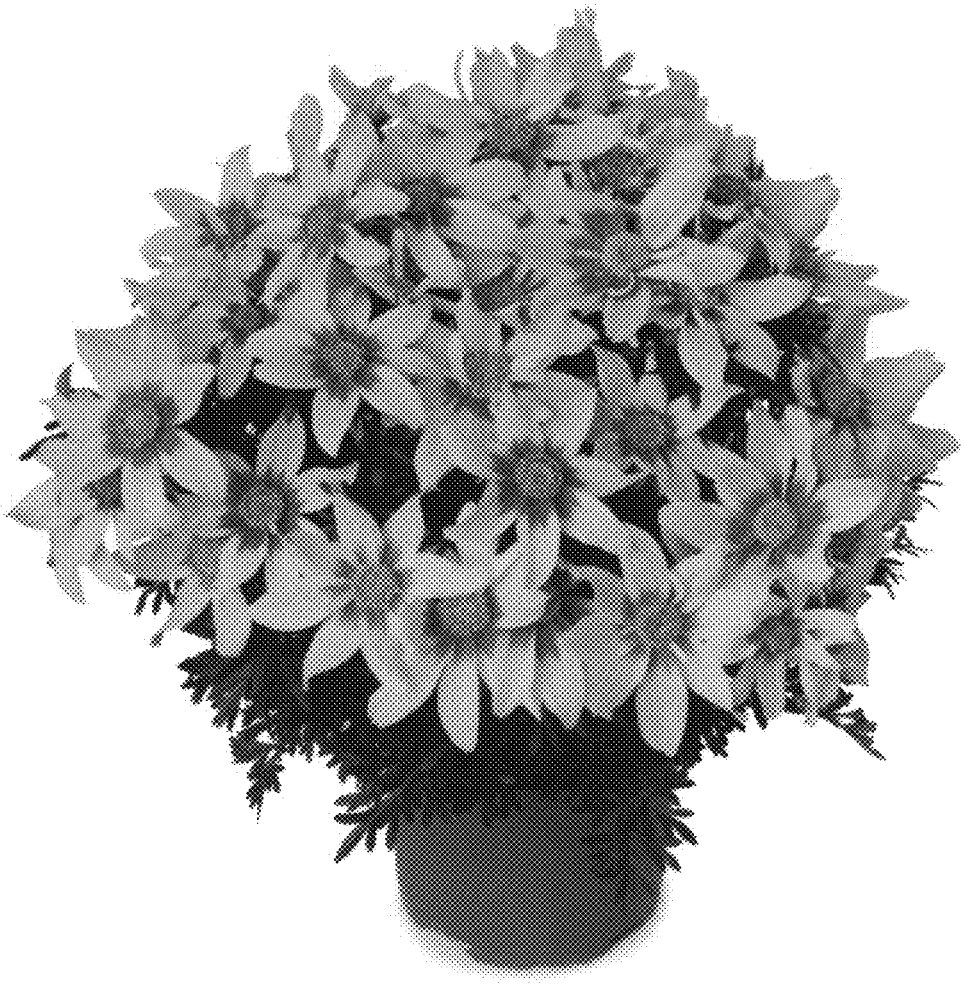
Figure 2:
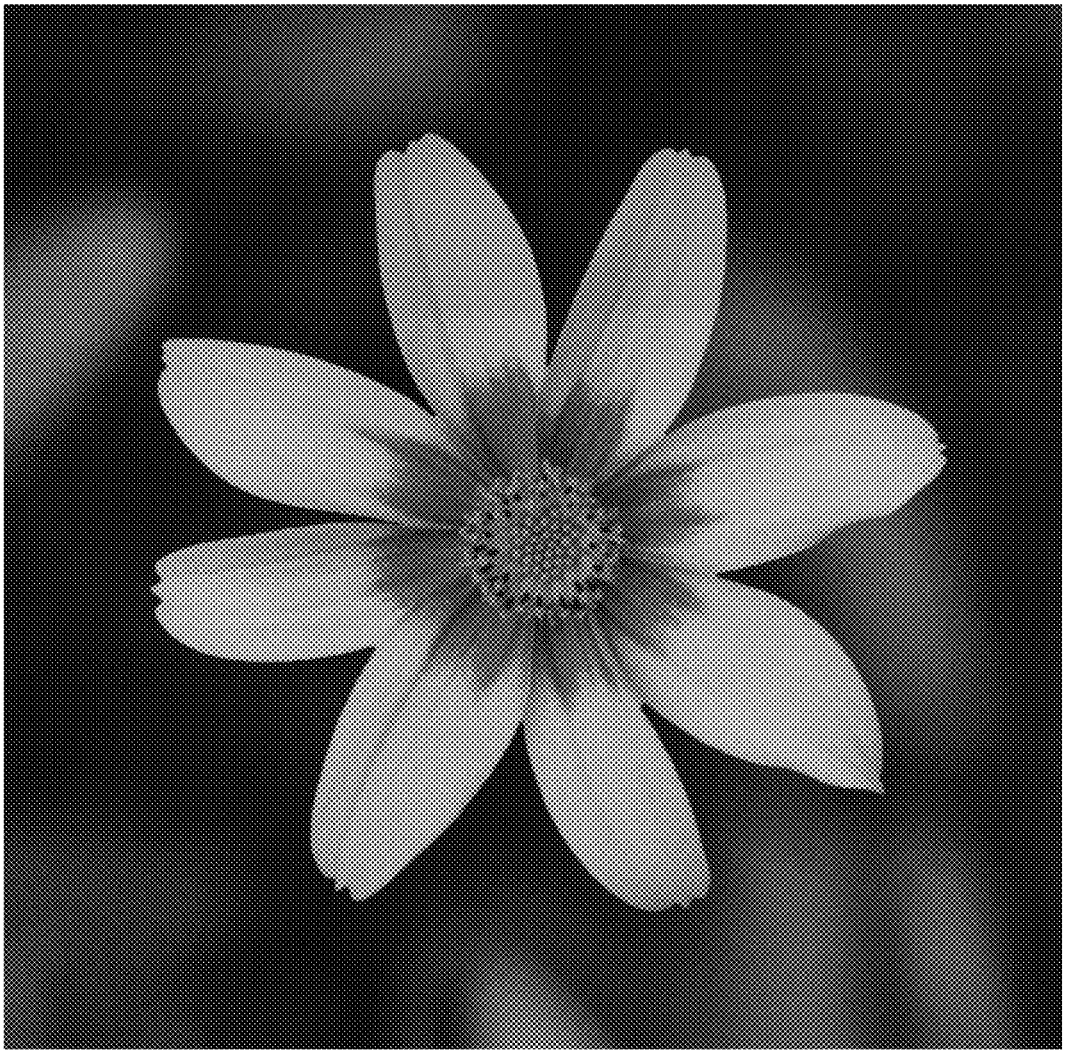

The photograph in FIG. 2 provides a close-up view of an inflorescence of 'FSK17S41'.

The colors in the photographs are as close as possible with the photographic and printing technology utilized and the color values cited in the detailed botanical description accurately describe the colors of the new *Bidens*.

DETAILED BOTANICAL DESCRIPTION

The following is a detailed description of 16-week-old plants of 'FSK17S41' as grown in 12-cm containers in a greenhouse in Andijk, The Netherlands. The phenotype of the new cultivar may vary with variations in environmental, climatic, and cultural conditions, as it has not been tested under all possible environmental conditions. The color determination is in accordance with The 2001 Colour Chart of The Royal Horticultural Society, London, England, except where general color terms of ordinary dictionary significance are used.

General description:

*Blooming period*.—Blooms continuously from spring through summer in Andijk, The Netherlands.

*Plant type*.—Evergreen perennial, grown as an annual.

*Plant habit*.—Mounding, rounded.

*Height and spread*.—An average of 17 cm in height and 28 cm in width as a 16-week-old plant.

*Hardiness*.—At least in U.S.D.A Zones 9 to 11.

*Diseases and pests*.—No susceptibility and resistance to pests and diseases has been observed.

*Root description*.—Fine, freely branching, 155B.

*Propagation*.—Stem cuttings.

*Root development*.—About 3 weeks to produce a rooted cutting and 8 weeks to produce a blooming plant from a rooted cutting.

*Growth rate*.—Moderately vigorous.

Stem description:

*Shape*.—Rounded, very slightly angled.

*Stem color*.—138B, spots on older stems 200C.

*Stem size*.—10 to 12 cm in length and 3 mm in diameter.

*Stem surface*.—Strongly pubescent with some anthocyanin presence.

*Stem strength*.—Strong.

*Internode length*.—2 to 5 cm.

*Branching habit*.—Freely branched, 7 to 9 stems per plant.

Foliage description:

*Leaf division*.—Simple.

*Leaf arrangement*.—Opposite.

*Leaf attachment*.—Petiolate.

*Leaf petioles*.—5 mm to 2 cm in length, 2 mm in diameter, 138B in color, surface slightly pubescent.

*Leaf shape*.—Ovate overall.

*Leaf margins*.—3-lobed with lobe margins entire.

*Leaf size*.—2 cm to 5 cm in length, 1.4 cm to 3 cm in width.

*Leaf base*.—Cuneate.

*Leaf apex*.—Acute.

*Leaf venation*.—Pinnate, color on upper and lower surface 137C.

*Leaf surface*.—Upper and lower surface smooth.

*Leaf color*.—Immature; upper surface 137C, lower surface 137D, mature; upper surface 137A, lower surface 137C.

Flower description:

*Inflorescence type*.—Terminal and axillary capitulums, daisy-type.

*Lastingness of inflorescence*.—Average of 7 to 8 days, discs persistent, ray florets self-cleaning.

*Fragrance*.—Sweet, a bit spicy.

*Quantity of inflorescences*.—Free flowering, with an average of 70 inflorescences with 11 buds per plant.

*Inflorescence size*.—An average of 5.5 cm to 6 cm in diameter, 1.2 cm in depth.

*Inflorescence buds*.—Ovate in shape, an average of 1.7 cm in depth, 7 mm in diameter, pubescent surface, color; 138A, top 12A.

*Peduncle*.—Rounded in shape, strong, 3.5 cm to 4 cm in length and 2 mm in diameter, 138B in color, surface is pubescent with short hairs.

Involucral bracts:

*Involucral number*.—16.

*Involucral arrangement*.—Spirally placed around involucrum.

*Involucral size*.—4 mm to 5 mm in length, 1.5 mm in width.

*Involucral color*.—Upper and lower surface 137A.

*Involucral texture*.—Both surfaces smooth.

*Involucral apex*.—Acute.

*Involucral base*.—Truncate.

*Involucral shape*.—Lanceolate.

*Involucral margins*.—Entire.

Ray florets (no reproductive organs):

*Number*.—7 to 8.

*Shape*.—Ovate.

*Size*.—An average of 2.5 cm in length and 1 cm in width.

*Apex*.—Tridentate.

*Base*.—Cuneate.

*Margins*.—Entire.

*Surface*.—Both surfaces smooth.

*Color*.—When opening and fully open upper surface; 12A, base 45A, when opening and fully open lower surface; 7B, just before senescence; upper surface 7A, base 171A, lower surface 7B.

Disc florets:

*Number*.—An average of 80.

*Shape*.—Tubular.

*Size*.—Average of 7 mm in length and 1.5 mm in width.

*Apex*.—Five-pointed.

*Margins*.—Entire.

*Base*.—Fused.

*Surface*.—Both surfaces smooth.

*Color*.—Upper and lower surface when fully open; 15A.

Reproductive organs (perfect):

*Presence*.—Disc florets only.

*Gynoecium*.—1 Pistil, an average of 3.5 mm in length, stigma; decurrent, 15A in color, style; 2.5 mm in length, ovary; 145D in color.

*Androecium*.—5 stamens, anther; basifixed, linear, 1 mm to 1.5 mm in length, 200A in color, filament; 1 cm in length, pollen; moderate in quantity, 21A in color.

*Seed*.—No seed development has observed to date.

It is claimed:

1. A new and distinct cultivar of *Bidens* plant named 'FSK17S41' as herein illustrated and described.

* * * * *